US012409139B2

United States Patent
Kocherlakota et al.

(10) Patent No.: US 12,409,139 B2
(45) Date of Patent: Sep. 9, 2025

(54) STABLE PARENTERAL FORMULATIONS OF DULOXETINE

(71) Applicant: LEIUTIS PHARMACEUTICALS LLP, Balanagar Hyderabad (IN)

(72) Inventors: Chandrashekhar Kocherlakota, Tarbund Secunderabad (IN); Nagaraju Banda, Kukatpally Hyderabad (IN); Santhosh Kumar Mankala, Old Bowenpally Hyderabad (IN); Suresh Pachaiyappan, Thiruvanmiyur Chennai (IN); Anji Reddy Keshireddy, Gajularamaram Hyderabad (IN)

(73) Assignee: LEIUTIS PHARMACEUTICALS LLP, Balanagar (IN)

( * ) Notice: Subject to any disclaimer, the term of this patent is extended or adjusted under 35 U.S.C. 154(b) by 0 days.

(21) Appl. No.: 18/386,863

(22) Filed: Nov. 3, 2023

(65) Prior Publication Data
US 2024/0058272 A1     Feb. 22, 2024

Related U.S. Application Data

(63) Continuation of application No. 17/778,906, filed as application No. PCT/IB2020/061263 on Nov. 30, 2020, now abandoned.

(51) Int. Cl.
  A61K 9/19      (2006.01)
  A61K 9/00      (2006.01)
  A61K 31/381    (2006.01)

(52) U.S. Cl.
  CPC .............. A61K 9/19 (2013.01); A61K 9/0019 (2013.01); A61K 31/381 (2013.01)

(58) Field of Classification Search
  CPC ....... A61K 9/19; A61K 31/381; A61K 9/0019
  See application file for complete search history.

(56) References Cited

U.S. PATENT DOCUMENTS 8,455,667 B2      6/2013  Sesha
2004/0223997 A1*  11/2004 Stogniew ............... A61P 31/10
                                                              424/405

(Continued)

FOREIGN PATENT DOCUMENTS

WO    00/051564 A1    9/2000
WO    03/105767 A2    12/2003
WO    2019/064185 A1  4/2019

OTHER PUBLICATIONS

Butreddy, A., Dudhipala, N., Janga, K.Y et al. Lyophilization of Small-Molecule Injectables: an Industry Perspective on Formulation Development, Process Optimization, Scale-Up Challenges, and Drug Product Quality Attributes. AAPS PharmSciTech 21, 252 https://doi.org/10.1208/s12249-020-01787-w) (Year: 2020).*

(Continued)

Primary Examiner — Benjamin J Packard
(74) Attorney, Agent, or Firm — Sughrue Mion, PLLC

(57) ABSTRACT

The present invention relates to a parenteral lyophilized formulation of duloxetine or a pharmaceutically acceptable salt thereof. Further, this invention relates to duloxetine dissolved in a suitable solvent system comprising one or more buffers, stabilizers, and other pharmaceutically acceptable excipients and subsequently lyophilized. The invention also describes combination formulation of Duloxetine with other active ingredients.

15 Claims, 1 Drawing Sheet

Permeability of various formulations evaluated using Rat Intestine at 15 minutes time (mcg/cm²)

(56) References Cited

U.S. PATENT DOCUMENTS

| | | | | |
|---|---|---|---|---|
| 2012/0196917 A1* | 8/2012 | Sesha | ............... | A61P 3/10 |
| | | | | 549/75 |
| 2015/0190403 A1* | 7/2015 | Cifter | ............... | A61K 31/138 |
| | | | | 514/220 |
| 2017/0129870 A1* | 5/2017 | Alapati | ............... | C07D 339/04 |

OTHER PUBLICATIONS

Kassim, Dina Y.; Esmat, Ibrahim M.1,; Elgendy, Mohammed A. 1. Impact of duloxetine and dexamethasone for improving postoperative pain after laparoscopic gynecological surgeries: A randomized clinical trial. Saudi Journal of Anaesthesia 12(1):p. 95-102, Jan.-Mar. 2018. | DOI: 10.4103/sja.SJA_519_17 (Year: 2018).*

Tang, Xiaolin, and Michael J. Pikal. "Design of freeze-drying processes for pharmaceuticals: practical advice." Pharmaceutical research 21 (2004): 191-200 (Year: 2004).*

Hippalgaonkar, Ketan et al. "Injectable lipid emulsions-advancements, opportunities and challenges." AAPS PharmSciTech vol. 11,4 (2010): 1526-40. doi:10.1208/s12249-010-9526-5). (Year: 2010).*

Baheti, Ankit; Kumar, Lokesh; Bansal, Arvind Kumar. Excipients used in lyophilization of small molecules. Journal of Excipients and Food Chemicals, [S.I.], v. 1, n. 1, p. 41-54, Jun. 2010. ISSN 21502668 (Year: 2010).*

Berge et al. Journal of Pharmaceutical Sciences, vol. 66, No. 1, Jan. 1977, pp. 1-19) (Year: 1977).*

International Search Report for PCT/IB2020/061263 dated Feb. 15, 2021 [PCT/ISA/210].

Written Opinion for PCT/IB2020/061263 dated Feb. 15, 2021 [PCT/ISA/237].

* cited by examiner

Permeability of various formulations evaluated using Rat Intestine at 15 minutes time (mcg/cm²)
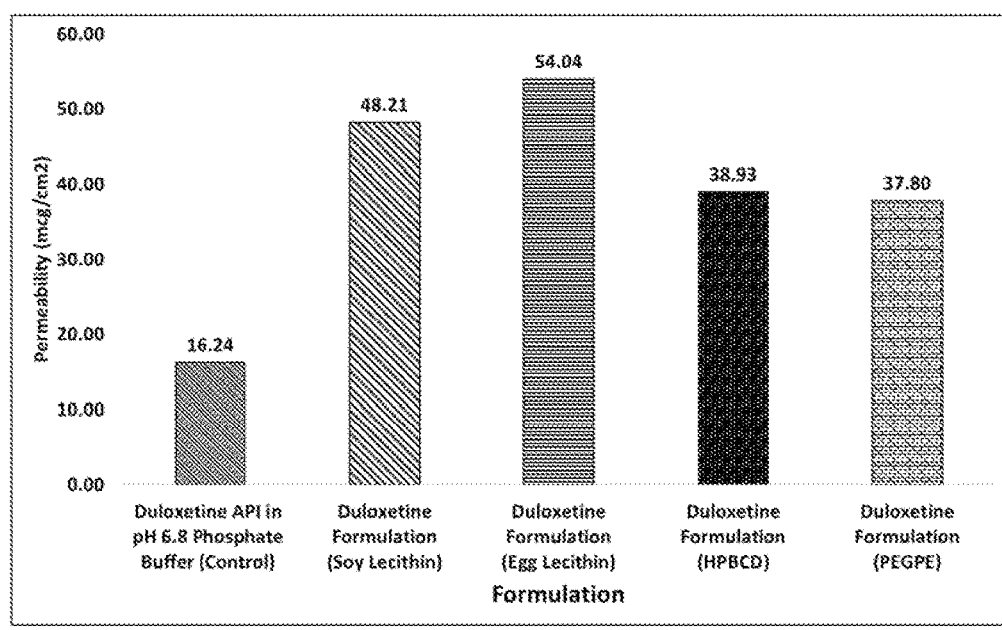

STABLE PARENTERAL FORMULATIONS OF DULOXETINE

CROSS REFERENCE TO RELATED APPLICATION

This application is a Continuation of U.S. application Ser. No. 17/778,906, filed on May 23, 2022, which is a 371 national stage application of International Application No. PCT/IB2020/061263, filed on Nov. 30, 2020, the disclosures of all of which are incorporated herein in their entirety.

FIELD OF THE INVENTION

The present invention relates to a parenteral dosage form of duloxetine or a pharmaceutically acceptable salt thereof and the method of manufacture of the said dosage form. The parenteral dosage form of this invention provides immediate relief to the patients.

BACKGROUND OF THE INVENTION

Duloxetine is a selective serotonin and norepinephrine reuptake inhibitor (SSNRI), chemically known as (+)-N-methyl-3-(1-naphthalenyloxy)-3-(2-thienyl) propan-1-amine). Duloxetine is not stable in presence of acid and degrades rapidly in acidic environment of the gastrointestinal tract. One of the degradant of acid hydrolysis is 1-napthol, which is known to be toxic and causes several side effects. To avoid the degradation and side effects, duloxetine is supplied as an enteric coated dosage form.

Duloxetine is commercially available in USA as delayed release capsules containing enteric coated duloxetine hydrochloride pellets. The product is sold under the brand name Cymbalta®. Duloxetine is used in the treatment of major depressive disorder, generalized anxiety disorder, diabetic peripheral neuropathic pain, fibromyalgia and chronic musculoskeletal pain. The Tia g (time for the absorption to begin) of duloxetine is 2 hours and Tmax (time to reach maximum concentration) is 6 to 10 hours. Hence the product is indicated to be administered 2 hours before the surgery for pain management.

The indications of duloxetine are such that quick onset of action is desirable. This is not possible with the currently available enteric coated formulation where the GI transit time is more than 6 hours. Further, the capsule formulation may present difficulties in swallowing in pediatric and elderly patients. This often leads to discontinuation of treatment and poor patient compliance.

There are patents describing oral formulations of duloxetine. For eg, U.S. Pat. No. 5,508,276 discloses an enteric duloxetine pellet formulation comprising a) a core consisting of duloxetine and a pharmaceutically acceptable excipient; b) an optional separating layer; c) an enteric layer comprising hydroxyl propyl methylcellulose acetate succinate (HPMCAS) and a pharmaceutically acceptable excipient. The patent describes the importance of formulating duloxetine as enteric coated pellets for better absorption and bioavailability but does not talk about parenteral formulations of duloxetine.

U.S. Pat. No. 8,758,779 discloses duloxetine powder for oral suspension whereas U.S. Pat. Nos. 8,455,667 and 8,513,439 disclose oral liquid compositions comprising duloxetine with suitable buffers. None of these patents have disclosures for making parenteral formulations.

The prior art formulations are associated with many disadvantages. Some of these are-increased time for absorption and onset of action for the enteric coated formulations, variability in drug absorption in different patients, difficulty in administering the formulations to patients who cannot take oral medication, pediatric and geriatric patients and possible degradation of the drug due to increased time of contact with gastric acids.

Thus, there is a need to make a parenteral formulation of duloxetine that can overcome the disadvantages associated in the prior art. These formulations are particularly advantageous because they result in quick action and relief from pain because the drug enters systemic circulation directly bypassing first pass metabolism and gastric acid degradation.

SUMMARY OF THE INVENTION

The present invention relates to a parenteral formulation of duloxetine comprising duloxetine dissolved in a suitable solvent system comprising one or more buffers, stabilizers and other pharmaceutically acceptable excipients. The formulation is in the form of a lyophilized injection comprising duloxetine.

BRIEF DESCRIPTION OF THE DRAWINGS

FIG. 01 shows Permeability of various formulations evaluated using Rat Intestine at 15 minutes time (mcg/cm$^2$).

DETAILED DESCRIPTION OF THE INVENTION

The term "duloxetine" is intended to refer to the pharmaceutically acceptable salts, solvates and polymorphs thereof. Duloxetine Hydrochloride is most preferred.

"Water Content" in the pharmaceutical formulation plays a major role in degrading the product. Drug gets degraded when it comes in contact with water, which ultimately effects the self-life of the product. The term "Water Content" in the present invention refers to an amount less than 5% w/w and more preferably less than 3% w/w even after 6 months of storage at accelerated conditions.

The words "Water Content" and Moisture Content" are interchangeable and means the same throughout the specification.

The term "lyophilize" in the context of this invention, is intended to refer to the process of freeze drying of a solution comprising duloxetine and other pharmaceutically acceptable excipients. The term "lyophilizate" refers to the product of lyophilization. The term "reconstitution" refers to dissolution of the lyophilizate for achieving a solution.

The inventors of the present invention defined the term "parenteral" formulation, which means a pharmaceutical formulation that can be administered through intravenous, intramuscular, subcutaneous, intraperitoneal and intrathecal routes of administration.

In one aspect, the present invention relates to a parenteral formulation of duloxetine for preoperative, peri-operative, post-operative pain management to reduce or alleviate need for Opioids and, therefore, opioid-related adverse effects or opioid-induced hyperalgesia, and for management of chronic and acute painful conditions.

The present inventors have now surprisingly found that it is possible to make a duloxetine lyophilized formulation that would overcome the disadvantages associated with prior art.

In one embodiment, the invention encompasses a lyophilized parenteral formulation of duloxetine.

Lyophilization or freeze-drying is a method for dehydrating samples used to preserve or increase stability or to stop degradation. Due to the low water content of lyophilized products, the action of microorganisms and enzymes is inhibited and the product life thereby increased. In lyophilization, the sample to be lyophilized is dissolved in an aqueous solution and subsequently frozen after which the surrounding pressure is reduced. The sample is then submitted to sublimation, optionally by the application of heat, in order to sublime the frozen water directly from the solid phase to the gas phase.

The lyophilized parenteral formulation of this invention comprises duloxetine dissolved in an aqueous vehicle and subsequently lyophilized in appropriate containers or glass vials. The lyophilizate thus formed can be reconstituted with a normal physiological solution like normal saline or with a specific diluent. The aqueous vehicle is preferably a sterile aqueous vehicle that is normally used as liquid vehicle for injection. Suitable aqueous vehicles include, for example, sterile water and sterile aqueous vehicles that contain suitable excipients that promote and preserve the stability of duloxetine after reconstitution.

In another embodiment, the invention relates to a lyophilized formulation comprising (i) duloxetine (ii) a bulking agent, (iii) an aqueous vehicle and (iv) other pharmaceutically acceptable excipients.

Bulking agents are used in lyophilization to increase product mass, adjust tonicity, improve product appearance, prevent product collapse, or aid in rehydration. Bulking agents for the purpose of this invention may be selected from mannitol, dextrose, cyclodextrin, sodium chloride, sorbitol and the like. Mannitol is the most preferred. The bulking agents ay make up 1-99% by weight of the lyophilized solid.

The aqueous vehicle can be selected from one or more of buffers selected from the group comprising acetate buffer, phosphate buffer, aspartic acid and boric acid buffer, citrate buffer and glycine buffer, succinate buffer, alanine buffer, valine buffer, histidine buffer, lactic acid buffer and the like. The aqueous vehicle can also contain mixture of process aid solvents like alcohols, acetonitrile, acetone and like that are removed during lyophilization.

The inventors carried out solubility/solution stability studies to determine the solution solubility of duloxetine in various buffers at different pH values. The concentration of the solution was kept at 10 mg/ml.

TABLE 1

Solubility data of duloxetine in various buffers at various pH

| Buffer | pH | Observation | Buffer | pH | Observation |
|---|---|---|---|---|---|
| Phosphate buffer | 4.5 | Clear solution | Serine buffer | 4.5 | Clear solution |
| Sodium phosphate buffer | 4.5 | Clear solution | | 5.5 | Clear solution |
| Acetate buffer | 4.5 | Clear solution | | 6.4 | Clear solution |
| | 5.5 | Clear solution | Lactic acid buffer | 4.5 | Clear solution |
| | 6.4 | Clear solution | | 5.5 | Clear solution |
| | 7.5 | Clear solution | | 6.4 | Clear solution |
| Aspartic acid and Boric acid buffer | 4.5 | Clear solution | | 7.5 | Clear solution |
| | 5.5 | Clear solution | Phosphate buffer | 5.5 | Insoluble |
| Succinate buffer | 4.5 | Clear solution | | 6.4 | Insoluble |
| Glycine buffer | 4.5 | Clear solution | Sodium phosphate buffer | 5.5 | Insoluble |
| | 5.5 | Clear solution | | 6.4 | Insoluble |
| | 6.4 | Clear solution | Citrate buffer | 4.5 | Insoluble |
| | 7.5 | Clear solution | | 5.5 | Insoluble |
| Alanine buffer | 4.5 | Clear solution | | 6.4 | Insoluble |
| | 5.5 | Clear solution | Aspartic acid and Boric acid buffer | 6.4 | Insoluble |
| Valine buffer | 4.5 | Clear solution | Succinate buffer | 5.5 | Insoluble |
| | 5.5 | Clear solution | | 6.4 | Insoluble |
| | 6.4 | Clear solution | Tris buffer | 4.5 | Insoluble |
| | 7.5 | Clear solution | | 5.5 | Insoluble |
| Leucine buffer | 4.5 | Clear solution | | 6.4 | Insoluble |
| | 5.5 | Clear solution | Alanine buffer | 6.4 | Insoluble |
| | 6.4 | Clear solution | Phenyl alanine buffer | 6.4 | Insoluble |
| | 7.5 | Clear solution | Lysine buffer | 4.5 | Insoluble |
| Isoleucine buffer | 4.5 | Clear solution | | 5.5 | Insoluble |
| | 5.5 | Clear solution | | 6.4 | Insoluble |
| | 6.4 | Clear solution | Histidine buffer | 4.5 | Insoluble |
| | 7.5 | Clear solution | | 5.5 | Insoluble |
| Methionine buffer | 4.5 | Clear solution | | 6.4 | Insoluble |
| | 5.5 | Clear solution | Tartaric acid buffer | 4.5 | Insoluble |
| | 6.4 | Clear solution | | 5.5 | Insoluble |
| | 7.5 | Clear solution | | 6.4 | Insoluble |
| Proline buffer | 4.5 | Clear solution | Meglumine buffer | 4.5 | Insoluble |
| | 5.5 | Clear solution | | 5.5 | Insoluble |
| | 6.4 | Clear solution | | 6.4 | Insoluble |
| | 7.5 | Clear solution | Serine buffer | 7.5 | Insoluble |
| Phenyl alanine buffer | 4.5 | Clear solution | 0.1N Sodium hydroxide buffer | 4.5 | Insoluble |
| | 5.5 | Clear solution | | 5.5 | Insoluble |
| Tryptophan buffer | 4.5 | Clear solution | | 6.4 | Insoluble |
| | 5.5 | Clear solution | | | |
| | 6.4 | Clear solution | | | |
| | 7.5 | Clear solution | | | |

The solution state stability of duloxetine was studied in various buffers for 24 hours. The data is tabulated below:

TABLE 2

Solution state stability of duloxetine in various buffers for 24 hours

| | Formulation | | | | | |
|---|---|---|---|---|---|---|
| | Glycine Buffer (pH-5.5) | Glycine Buffer (pH-6.4) | Acetate Buffer (pH-5.5) | Acetate Buffer (pH-6.4) | Aspartic acid + Boric Acid Buffer (pH-5.5) | Aspartic acid + Boric Acid Buffer (pH-6.4) |
| | | | Condition-RT-25° C. | | | |
| | I*  24 h | I*  24 h | I*  24 h | I*  24 h | I*  24 h | I*  24 h |
| pH | 5.59  5.5 | 6.23  6.35 | 5.32  5.4 | 6.38  6.1 | 5.8  5.7 | 6.6  6.5 |
| Assay (%) | 105  104.8 | 97.7  96.6 | 93.9  92.4 | 94.3  90.3 | 93.0  93.3 | 97.9  97.8 |
| Total Impurities | 0.12  0.2 | 0.10  0.18 | 0.14  0.2 | 0.1  0.1 | 0.3  0.5 | 0.3  0.5 |

Note:
I*: Initial

The samples were stored for 24 hours and analyzed for pH, assay and total impurities by standard analytical procedures. The data showed that duloxetine has satisfactory stability in all the buffers tested. The acetate buffer at pH-5.5 and pH-6.4 and the glycine buffer at pH-5.5 and pH-6.4 showed best results in terms of assay and total impurities.

In yet another embodiment, the invention relates to a lyophilized formulation comprising (i) duloxetine, (ii) a bulking agent, (iii) an aqueous vehicle, (iv) a stabilizer and (v) other pharmaceutically acceptable excipients.

In yet another embodiment, the invention relates to a lyophilized formulation comprising (i) duloxetine, (ii) a bulking agent (iii) an aqueous vehicle, (iv) a stabilizer, (v) one or more pH adjusting agents and (vi) other pharmaceutically acceptable excipients.

In yet another embodiment, the invention relates to a lyophilized formulation comprising (i) duloxetine, (ii) a bulking agent (iii) an aqueous vehicle, (iv) a stabilizer, (v) one or more surfactants and (vi) other pharmaceutically acceptable excipients.

The lyophilized formulation of the present invention has less than 0.5% w/w of each of the following impurities: duloxetine 4-napthyl isomer ((4-[3-(Methylamino)-1-(thiophen-2-yl)propyl]naphthalen-1-ol), alpha napthol ((Naphthalen-1-ol)), duloxetine beta napthol-1-yl isomer ((2-[3-(Methylamino)-1-(thiophen-2-yl)propyl]naphthalen-1-ol)). More specifically the above said impurities are less than 0.3% w/w each, even after 6 months of storage under accelerated conditions.

The stabilizer in the formulation can be selected from one or more of DOTA, DTPA, EDTA and the like. The quantity of the stabilizer can be from 0.001% w/w to 10% w/w.

The one or more pH adjusting agents can be selected from the group comprising sodium hydroxide, hydrochloric acid, mineral acids, carboxylic acids and salts thereof.

The surfactants may be selected from the group comprising lecithin, soya lecithin, egg lecithin, PEG-PE, phosphatidyl choline, etc.

In yet another embodiment, the invention relates to a kit comprising lyophilized formulation of duloxetine supplied together with a diluent. The diluent supplied in the kit can be selected from water for injection, dextrose solution, normal saline, mannitol solution, dextrose normal saline solution (DNS), half saline solution (with a concentration of sodium chloride at 0.45% w/v), dextrose 5%, Normal saline with Arginine (pH 10.07), Ringer Lactate solution.

The lyophilized formulation of the present invention can be reconstituted with the diluent solution described above. It can be administered directly after reconstitution or may further be diluted with any of the physiologically acceptable solutions at the time of administration.

The lyophilized samples prepared as per the invention were reconstituted with water and normal saline.

TABLE 3

Reconstitution studies of duloxetine lyophilized samples

| Batch | Reconstituted media | Initial pH | Observation |
|---|---|---|---|
| 1A | Water | 4.55 | Clear solution |
| 1B | | 5.56 | Clear solution |
| 1C | | 6.22 | Clear solution |
| 1D | | 4.64 | Clear solution |
| 1E | | 5.43 | Clear solution |
| 1F | | 6.11 | Clear solution |
| 1G | | 4.62 | Clear solution |
| 1 H | | 5.17 | Clear solution |
| 1I | | 6.02 | Clear solution |
| 1A | 0.9% Sodium chloride | 4.51 | Clear solution |
| 1B | | 5.52 | Clear solution |
| 1C | | 6.14 | Clear solution |
| 1D | | 4.63 | Clear solution |
| 1E | | 5.43 | Clear solution |
| 1F | | 6.13 | Clear solution |
| 1G | | 4.6 | Slightly hazy |
| 1 H | | 5.09 | Clear solution |
| 1I | | 6.07 | Clear solution |
| 316A | 0.45% Sodium Chloride | 6.12 | Clear solution |
| 316A | Dextrose 5% | 5.97 | Clear solution |
| 316A | Dextrose Normal Saline | 5.77 | Clear solution |
| 316A | Normal saline with Arginine (pH 10.07) | 7.24 | Clear solution |
| 316A | Ringer Lactate | 6.30 | Clear solution |

The formulations were observed to be clear upon reconstitution with water, 0.9% Sodium chloride, 0.45% Sodium Chloride, Dextrose 5% Dextrose Normal Saline Normal saline with Arginine (pH 10.07) Ringer Lactate.

All the formulations showed satisfactory description and desired pH range.

Manufacturing Process

The subject-matter of the present invention further relates to a process for preparing the lyophilized formulation and the kit. The process comprises the steps of:
(i) mixing the following components (in any suitable order): duloxetine or a pharmaceutically acceptable salt or solvates thereof; an aqueous vehicle; one or more bulking agents; optionally one or more stabilizers; and optionally one or more pH adjusting agents; to provide for an aqueous preparation, wherein duloxetine has a concentration of 1 to 20% w/v, based on the aqueous preparation;

(ii) lyophilizing the aqueous preparation to provide for the lyophilized formulation in solid form; and optionally (iii) preparing the diluent and filling in suitable containers or vials; and optionally (iv) providing the lyophilized formulation and diluent in the form of a kit.

The aqueous preparation may be a suspension/dispersion or solution.

The lyophilization step may be carried out in vials, blisters or in any other larger vessel, such as stainless-steel trays or tanks, called "bulk lyophilization".

The bulk solution prepared in step (i) was evaluated for stability. The data is tabulated below. Stability of bulk solution is important to ensure a quality product even in the case unforeseen prolonged process times. Various concentrations of the drug i.e 10 mg/ml, 20 mg/ml and 30 mg/ml were studied in different pH ranges. The formulations were prepared as per the details of example 1.

Stability Data of Bulk Solution Up to 24 h.

TABLE 4A

Stability of bulk solution at a concentration of 10 mg/ml

| | B. NO | | | | | | | | |
|---|---|---|---|---|---|---|---|---|---|
| | 1A | | | 1B | | | 1C | | |
| Condition | Initial | 24 h 2-8° C. | 24 h 25° C. | Initial | 24 h 2-8° C. | 24 h 25° C. | Initial | 24 h 2-8° C. | 24 h 25° C. |
| Description | | | | Clear and Colourless Solution | | | | | |
| Assay (%) | 101.9 | 101.9 | 102.0 | 103.4 | 101.4 | 102.0 | 102.4 | 101.9 | 102.4 |
| Related substances | | | | | | | | | |
| Impurity Name | | | | | % w/w | | | | |
| Duloxetine Alcohol | 0.01 | 0.01 | 0.02 | ND | ND | ND | ND | ND | ND |
| Duloxetine Napthol 4-yl isomer | 0.02 | 0.02 | 0.07 | 0.01 | 0.01 | 0.03 | 0.01 | 0.01 | 0.02 |
| Alpha Napthol | 0.03 | 0.03 | 0.12 | 0.01 | 0.01 | 0.02 | 0.01 | 0.01 | 0.01 |
| Duloxetine Beta napthol-1-yl isomer | 0.02 | 0.02 | 0.07 | 0.01 | 0.01 | 0.04 | 0.01 | 0.01 | 0.02 |
| Duloxetine Related Compound-F | 0.05 | 0.05 | 0.05 | 0.06 | 0.06 | 0.06 | 0.06 | 0.06 | 0.04 |
| Total Impurities (%) | 0.13 | 0.13 | 0.33 | 0.09 | 0.09 | 0.15 | 0.09 | 0.09 | 0.09 |

TABLE 4B

Stability of bulk solution at a concentration of 20 mg/ml

| | B. NO | | | | | | | | |
|---|---|---|---|---|---|---|---|---|---|
| | 1D | | | 1E | | | 1F | | |
| Condition | Initial | 24 h 2-8° C. | 24 h 25° C. | Initial | 24 h 2-8° C. | 24 h 25° C. | Initial | 24 h 2-8° C. | 24 h 25° C. |
| Description | | | | Clear and Colourless Solution | | | | | |
| Assay (%) | 102.1 | 101.4 | 101.8 | 103.2 | 101.2 | 102.1 | 102.7 | 101.2 | 102.0 |
| Related substances | | | | | | | | | |
| Impurity Name | | | | | % w/w | | | | |
| Duloxetine Alcohol | 0.01 | 0.01 | 0.03 | ND | ND | 0.01 | ND | ND | ND |
| Duloxetine Napthol 4-yl isomer | 0.02 | 0.02 | 0.08 | 0.01 | 0.01 | 0.04 | 0.01 | 0.01 | 0.02 |
| Alpha Napthol | 0.05 | 0.04 | 0.18 | 0.02 | 0.02 | 0.05 | 0.01 | 0.01 | 0.01 |
| Duloxetine Beta napthol-1-yl isomer | 0.02 | 0.02 | 0.10 | 0.01 | 0.02 | 0.05 | 0.01 | 0.01 | 0.03 |
| Duloxetine Related Compound-F | 0.06 | 0.06 | 0.06 | 0.06 | 0.06 | 0.06 | 0.06 | 0.06 | 0.06 |
| Total Impurities (%) | 0.16 | 0.15 | 0.46 | 0.10 | 0.11 | 0.21 | 0.09 | 0.09 | 0.12 |

TABLE 4C

Stability of bulk solution at a concentration of 30 mg/ml

|  | B. NO | | | | | | | | |
|---|---|---|---|---|---|---|---|---|---|
|  | 1G | | | 1H | | | 1I | | |
| Condition | Initial | 24 h 2-8° C. | 24 h 25° C. | Initial | 24 h 2-8° C. | 24 h 25° C. | Initial | 24 h 2-8° C. | 24 h 25° C. |
| Description | | | | Clear and Colourless Solution | | | | | |
| Assay (%) | 101.4 | 101.7 | 101.9 | 101.6 | 101.4 | 103.0 | 101.1 | 101.3 | 102.0 |
| Related substances | | | | | | | | | |
| Impurity Name | | | | % w/w | | | | | |
| Duloxetine Alcohol | ND | 0.01 | 0.03 | ND | ND | 0.01 | ND | ND | ND |
| Duloxetine Napthol 4-yl isomer | 0.02 | 0.02 | 0.08 | 0.01 | 0.01 | 0.03 | 0.01 | 0.01 | 0.02 |
| Alpha Napthol | 0.03 | 0.03 | 0.16 | 0.01 | 0.01 | 0.05 | 0.01 | 0.01 | 0.02 |
| Duloxetine Beta napthol-1-yl isomer | 0.01 | 0.02 | 0.09 | 0.01 | 0.01 | 0.04 | 0.01 | 0.01 | 0.03 |
| Duloxetine Related Compound-F | 0.06 | 0.06 | 0.06 | 0.06 | 0.06 | 0.06 | 0.06 | 0.06 | 0.06 |
| Total Impurities (%) | 0.12 | 0.14 | 0.42 | 0.09 | 0.09 | 0.19 | 0.09 | 0.09 | 0.13 |

It is evident from the data above that the stability of bulk solution is satisfactory across the pH ranges of 4.5, 5.5 and 6.4 at temperatures of 2-8° c. and 25° c. There is practically no loss in the percentage of drug after 24 hours and no increase in impurities.

In Vitro Ex In-Vivo Permeability Study

For administration of drug through intramuscular, subcutaneous, intraperitoneal, intrathecal, inhalation, and intranasal routes of administration, permeability of drug from the formulation plays a significant role. Thus various formulations were evaluated for permeability flux rate of Duloxetine using invitro ex-vivo rat intestine.

Details of In-Vitro and Ex-Vivo Permeation Study:

a. Experimental Setup:

1. Permeability Barrier Setup (Intestine Preparation):

Wistar Rats of Body weight of 300 (±25) grams were selected and fasted overnight for 12 hours before sacrificing. The animals were sacrificed by cervical dislocation and intestinal segments (jejunum portion) were isolated. The isolated intestine segments were washed with Ringer lactate solution then stored in aerated Ringer solution till usage. 20 cms of intestine segment was selected to fill 2 mL of the sample. Both the ends of the segments were tied with cotton thread ensuring no leakage from the surface and subjected for diffusion study for determining permeability.

2. Sample Preparation:

The formulation of examples of 8A, 16, 17, 6 and 18 were diluted to get concentration of 5 mg/mL of duloxetine in phosphate buffer pH 6.8. 2 mL of each solution was taken in separate.

Wherein above examples contain: (Example 8A; soya lecithin), (Example 16; Egg Lecithin), (Example 17: HPBCD), (Example 6: PEGPE) and Duloxetine API—(Example 18))

3. Experimental Condition and Permeability Evaluation:

Diffusion study was performed by placing the intestine segments in 50 mL of oxygenated 6.8 pH phosphate buffer at 37±0.5° C. temperature under rotary shaking at 50 rpm. The intestine acts as donor chamber and diffusion media acts as receptor chamber from which aliquot samples were collected at predefined time points.

4. Sample Collection:

The sample were collected at 15 mins, 30 mins, 45 mins, 1 Hrs, 2 Hrs, 3 Hrs, 6 Hrs, 12 Hrs, 24 Hrs and 48 Hrs. At each time point 1 mL of the sample was collected from the diffusion phase and replaced with equal volume of phosphate buffer of temperature 37±0.5° C. temperature. The samples were analysed using HPLC method for Duloxetine content.

b. Data Evaluation:

The samples collected at each time point were analysed for diffused drug content by HPLC method. The flux rates were calculated from slope of a trend-line plotted by taking cumulative amount drug release form unit surface area (i.e. mcg/cm2) against time (h). The flux rates were calculated using the following equation (1):

$$J = m/At \qquad \text{Equation (1)}$$

Where:

J=is the Flux of compound "m" moving through a cross-sectional area "A" during time "t"

TABLE 5

Study summary

| S. No | Sample ID/ Details | Description of sample | Drug conc. in the intestinal sac/ Volume | Flux rate calculated (mcg/cm$^2$) at 15$^{th}$ minute | Remarks |
|---|---|---|---|---|---|
| 1 | Duloxetine API in pH 6.8 Phosphate buffer | Drug dissolved in phosphate buffer without any excipients | 2 mL of 5 mg/mL solution (10 mg of Drug in Sac) | 16.24 mcg/cm$^2$ | Control: API in pH 6.8 Phosphate Buffer |
| 2 | Duloxetine formulation with Soy lecithin | Lyophilized duloxetine formulation with Soy lecithin | 2 mL of 5 mg/mL solution (10 mg of Drug in Sac) | 48.21 | Permeability improved >3 folds over API in buffer |
| 3 | Duloxetine formulation with Egg lecithin | Lyophilized duloxetine formulation with Egg lecithin | 2 mL of 5 mg/mL solution (10 mg of Drug in Sac) | 54.04 | Permeability improved >3 folds over API in buffer |
| 4 | Duloxetine formulation with HPBCD | Lyophilized duloxetine formulation with HPBCD | 2 mL of 5 mg/mL solution (10 mg of Drug in Sac) | 38.93 | Permeability improved >2 folds over API in buffer |
| 5 | Duloxetine formulation with PEG-PE | Lyophilized duloxetine formulation with PEGPE | 2 mL of 5 mg/mL solution (10 mg of Drug in Sac) | 37.80 | Permeability improved >2 folds over API in buffer |

Accompanying FIG. 1 illustrates Permeability of various formulations evaluated using Rat Intestine at 15 minutes time (mcg/cm2). The permeability flux rate of duloxetine formulation containing Lecithin's or PEG-PE or Cyclodextrin was found to be increased by 2-3 folds than compared to flux rates of drug solution that does not have any of these excipients.

Duloxetine Combination Formulations

American Pain Society guidelines on management of acute pain and Chronic Non-cancer pain suggests "multi-modal analgesia" or "balanced analgesia" for the treatment of postoperative pain management. Multimodal or Balanced Analgesia includes involves the use of more than one method or modality of controlling pain (e.g., drugs from two or more classes, drug plus nondrug treatment) to obtain additive beneficial effects, reduce side effects, or both.

Nearly 50% of the patients who visit hospitals due to pain related illness suffer from acute neuropathic pain, chronic neuropathic pain, post amputation pain, cancer surgeries, post traumatic limb pain and neuropathic pain due to trauma. It would be advantageous to have a parenteral formulation with a combination of another active ingredient like paracetamol or diclofenac or the like with duloxetine that would address the treatment need in such patients. For painful phases of chronic pain management, a short duration of parenteral product usage for quick response s very much desired.

In yet another embodiment, the invention also encompasses an injection formulation comprising (i) duloxetine or a pharmaceutically acceptable salt thereof, and (ii) a second active ingredient, selected from the group comprising paracetamol, diclofenac, gabapentin, pregabalin, dexamethasone, lidocaine, melatonin etc.

The following Examples are intended to illustrate the present invention and are not to be considered as limiting the scope of the invention.

Example 1

| | | Quantity % w/v | | | | | | | | |
|---|---|---|---|---|---|---|---|---|---|---|
| S. No | Ingredients | 1A | 1B | 1C | 1D | 1E | 1F | 1G | 1H | 1I |
| 1. | Duloxetine Hydrochloride | 5.00 | 5.00 | 5.00 | 5.00 | 5.00 | 5.00 | 5.00 | 5.00 | 5.00 |
| 2. | Mannitol | 10.0 | 10.0 | 10.0 | 10.0 | 10.0 | 10.0 | 10.0 | 10.0 | 10.0 |
| 3. | DOTA* | 0.02 | 0.02 | 0.02 | 0.02 | 0.02 | 0.02 | 0.02 | 0.02 | 0.02 |
| 4. | 5.0N Sodium hydroxide Solution | 0.02 | 0.46 | 0.60 | 0.19 | 0.84 | 1.06 | 0.96 | 1.06 | 1.14 |
| 5. | Acetate buffer (10 mg/mL) | 84.9 | 84.5 | 84.3 | 84.7 | 84.1 | 83.92 | 84.02 | 83.9 | 83.8 |
| | pH | 4.5 | 5.5 | 6.4 | 4.5 | 5.5 | 6.4 | 4.5 | 5.5 | 6.4 |

*DOTA—Dodecane tetra acetic acid

Manufacturing Process 1. 80% of required quantity of vehicle for batch is taken in a vessel.
2. Duloxetine was transferred to the above vessel and dissolved by stirring at 400 rpm till the solution turned clear.
3. Mannitol was added to the above drug solution and stirred for 3 minutes till the solution becomes clear.
4. To the above solution, DOTA is added and stirred well for 1 minute till the solution turned clear.
5. The pH of the bulk solution is adjusted by using 5.0N Sodium hydroxide Solution 6. The final volume of the above solution is adjusted with remaining quantity of water for Injection.
7. The bulk solution is filled into vials and lyophilized.

Example 2

| S. No | Ingredients | Qty/vial (mg) | Qty % w/v |
|---|---|---|---|
| 1. | Duloxetine Hydrochloride | 56.30 | 3.75 |
| 2. | Dextrose monohydrate | 50.00 | 3.33 |
| 3. | DOTA* | 0.30 | 0.02 |
| 4. | 0.1N Sodium hydroxide Solution | 0.003 | 0.0002 |
| 5. | Glycine solution (0.5 mg/mL) Q.s | 1393.40 | 92.89 |

*DOTA—Dodecane tetra acetic acid

Manufacturing Process
1. 80% of required quantity of vehicle for batch is taken in a vessel.
2. Duloxetine was transferred to the above vessel and dissolved by stirring at 400 rpm till the solution turned clear.
3. Dextrose monohydrate was added to the above drug solution and stirred for 3 minutes till the solution becomes clear.
4. To the above solution, DOTA is added and stirred well for 1 minute till the solution turned clear.
5. The pH of the bulk solution is adjusted to 5.5 by using 0.1 N Sodium hydroxide Solution.
6. The final volume of the above solution is adjusted with remaining quantity of water for Injection.
7. The bulk solution is filled into vials and lyophilized.

Example 3

| | | Example 3A | | Example 3B | | Example 3C | |
|---|---|---|---|---|---|---|---|
| S. No | Ingredients | Qty/vial (mg) | Qty % w/v | Qty/Vial (mg) | Qty % w/v | Qty/vial (mg) | Qty % w/v |
| 1. | Duloxetine Hydrochloride | 30.0 | 4.0 | 60.0 | 4.0 | 90.0 | 4.0 |
| 2. | Mannitol | 60.0 | 8.0 | 120.0 | 8.0 | 180.0 | 8.0 |
| 3. | DOTA* | 0.15 | 0.02 | 0.3 | 0.02 | 0.45 | 0.02 |
| 4. | 5N Sodium hydroxide Solution | 6.78 | 0.9 | 13.5 | 0.9 | 20.3 | 0.9 |
| 5. | Acetate buffer (20 mg/mL) | Q.s to 0.75 mL | 87.08 | Q.s to 1.5 mL | 87.08 | Q.s to 2.25 mL | 87.08 |

*DOTA—Dodecane tetra acetic acid

Manufacturing Process
1. 80% of required total batch quantity of vehicle was dispensed and taken in a vessel.
2. Dispensed quantity of API was transferred to the above vessel and dissolved by stirring at 400 rpm till the solution turned clear.
3. Dispensed quantity of Mannitol was added to the above drug solution and stirred for 3 minutes till the solution become clear.
4. To the above solution dispensed quantity of stabilizer (DOTA) was added and stirred well for 1 minute till the solution turned clear.
5. The pH of the bulk solution was adjusted to 5.5 by using 5N Sodium hydroxide solution.
6. Final volume of the above solution was adjusted with remaining quantity of Vehicle.

The formulations were studied for stability.

Stability Study of Duloxetine Formulations

TABLE 6A

Stability study of duloxetine formulation at 30 mg concentration

| B. NO | | | 3A | | |
|---|---|---|---|---|---|
| Condition | Initial | 4 W-2-8° C. | 4 W-25° C. | 4 W-30° C. | 4 W-40° C. |
| Strength | | | 30 mg/vial | | |
| Description | | | White Lyophilized Powder | | |
| Impurity Name | | | % w/w | | |
| Duloxetine Alcohol | ND | ND | ND | ND | 0.01 |
| Duloxetine Napthol 4-yl isomer | 0.01 | 0.01 | 0.01 | 0.01 | 0.03 |
| Alpha Napthol | 0.02 | 0.02 | 0.02 | 0.02 | 0.03 |
| Duloxetine Beta napthol-1-yl isomer | 0.01 | 0.01 | 0.02 | 0.02 | 0.06 |

TABLE 6A-continued

Stability study of duloxetine formulation at 30 mg concentration

| Total Impurities (%) | 0.11 | 0.09 | 0.13 | 0.17 | 0.53 |
|---|---|---|---|---|---|
| Assay | 103.6 | 101.8 | 101.9 | 101.3 | 101.9 |
| Water Content (mg/Vial) | 4.6 | 4.6 | 6.2 | 14.1 | 7.7 |

Note:
ND—Not determined,
W—Week

TABLE 6B

Stability study of duloxetine formulation at 60 mg concentration

| | B. NO 3B Condition | | | | |
|---|---|---|---|---|---|
| | Initial | 4 W-2-8° C. | 4 W-25° C. | 4 W-30° C. | 4 W-40° C. |
| | | | Strength | | |
| | | | 60 mg/vial | | |
| | | | Description | | |
| | | | White Lyophilized Powder | | |
| Impurity Name | | | % w/w | | |
| Duloxetine Alcohol | ND | ND | ND | 0.01 | 0.01 |
| Duloxetine Napthol 4-yl isomer | 0.01 | 0.01 | 0.01 | 0.03 | 0.10 |
| Alpha Napthol | 0.02 | 0.02 | 0.02 | 0.03 | 0.07 |
| Duloxetine Beta napthol-1-yl isomer | 0.01 | 0.01 | 0.02 | 0.06 | 0.28 |
| Total Impurities (%) | 0.11 | 0.09 | 0.13 | 0.53 | 1.66 |
| Assay | 102.9 | 102.0 | 101.9 | 100.6 | 96.8 |
| Water Content (mg/Vial) | 9.1 | 8.4 | 11.7 | 10.6 | 10.7 |

Note:
ND—Not determined,
W—Week

TABLE 6C

Stability study of duloxetine formulation at 90 mg concentration

| | B. NO 3C Condition | | | | |
|---|---|---|---|---|---|
| | Initial | 4 W-2-8° C. | 4 W-25° C. | 4 W-30° C. | 4 W-40° C. |
| | | | Strength | | |
| | | | 90 mg/vial | | |
| | | | Description | | |
| | | | White Lyophilized Powder | | |
| Impurity Name | | | % w/w | | |
| Duloxetine Alcohol | ND | ND | ND | ND | 0.01 |
| Duloxetine Napthol 4-yl isomer | 0.01 | 0.01 | 0.01 | 0.01 | 0.03 |
| Alpha Napthol | 0.02 | 0.02 | 0.02 | 0.02 | 0.03 |
| Duloxetine Beta napthol-1-yl isomer | 0.01 | 0.01 | 0.02 | 0.02 | 0.07 |
| Total Impurities (%) | 0.11 | 0.09 | 0.13 | 0.17 | 0.54 |
| Assay | 100.8 | 100.0 | 101.8 | 99.7 | 101.4 |
| Water Content (mg/Vial) | 12.5 | 10.8 | 6.2 | 14.1 | 18.5 |

Note:
ND—Not determined,
W—Week

Example 4

| S. No | Ingredients | Qty/vial (mg) | Qty % w/v |
|---|---|---|---|
| 1. | Duloxetine Hydrochloride | 60.00 | 4.00 |
| 2. | Mannitol | 120.00 | 8.00 |
| 3. | DOTA | 0.30 | 0.02 |
| 4. | Acetic acid | 10.00 | 0.67 |
| 5. | 5N Sodium hydroxide Solution | 3.00 | 0.20 |
| 6. | Glycine solution (10 mg/mL) Q.s | Q.s 1.5 mL | 87.11 |

Manufacturing Process
1. 80% of required total batch quantity of glycine solution was dispensed and taken in a vessel.
2. Dispensed quantity of API was transferred to the above vessel and dissolved by stirring at 400 rpm till the solution turned clear.
3. Dispensed quantity of Mannitol was added to the above drug solution and stirred for 3 minutes till the solution become clear.
4. To the above solution dispensed quantity of stabilizer (DOTA/Acetic acid) was added and stirred well for 1 minute till the solution turned clear.
5. The pH of the bulk solution was adjusted to 5.5 by using 5N Sodium hydroxide solution.
6. The bulk solution was lyophilized after filling into vials

Example 5

| S. No | Ingredients | Qty/vial (mg) | Quantity % w/v |
|---|---|---|---|
| 1. | Duloxetine Hydrochloride | 60.00 | 4.00 |
| 2. | Mannitol | 120.00 | 8.00 |
| 3. | DOTA | 0.30 | 0.02 |
| 4. | Acetic acid | 10.00 | 0.67 |
| 5. | 5N Sodium hydroxide Solution | 3.00 | 0.20 |
| 6. | Serine solution (10 mg/mL) | Q.s 1.5 mL | 87.94 |

Manufacturing Process
1. 80% of required total batch quantity of Serine solution was dispensed and taken in a vessel.
2. Dispensed quantity of API was transferred to the above vessel and dissolved by stirring at 400 rpm till the solution turned clear.
3. Dispensed quantity of Mannitol was added to the above drug solution and stirred for 3 minutes till the solution become clear.
4. To the above solution dispensed quantity of stabilizer (DOTA/Acetic acid) was added and stirred well for 1 minute till the solution turned clear.
5. The pH of the bulk solution was adjusted to 5.5 by using 5N Sodium hydroxide solution.
6. The bulk solution was lyophilized after filling into vials.

Example 6

| S. No | Ingredients | Qty (mg/mL) | Qty % w/v | Qty % w/w |
|---|---|---|---|---|
| 1. | Duloxetine Hydrochloride | 30.0 | 3 | 31.40 |
| 2. | Mannitol | 45.0 | 4.5 | 47.10 |
| 3. | EDTA | 0.2 | 0.02 | 0.20 |
| 4. | Lipoid PE 18:0/18:0-PEG-2000 | 10.0 | 1.0 | 10.46 |
| 5. | L-Histidine | Q.s to pH 6.0 | Q.s to pH 6.0 | 0.34 |
| 6. | 1% Glycine solution | Q.s to 1 mL | Q.s to 100% | 10.46 |

Manufacturing Process
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid PE 18:0/18:0-PEG-2000 was transferred and stirred for 15 minutes at 450 rpm to obtain a clear solution.
3. To the above solution dispensed quantity of duloxetine was added and stirred for 30 minutes at 400 rpm for obtaining a clear solution.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.0±0.1 using L-histidine.
7. Final volume of the bulk solution was adjusted to desired level with remaining amount of 1% glycine solution.
8. The bulk solution was lyophilized after filling into vials.

Example 7

| S. No | Ingredients | Qty (mg/mL) | Qty % w/v | Qty % w/w |
|---|---|---|---|---|
| 1. | Duloxetine Hydrochloride | 30.00 | 3 | 30.864 |
| 2. | Mannitol | 45.00 | 4.5 | 46.296 |
| 3. | EDTA | 0.20 | 0.02 | 0.2058 |
| 4. | Lipoid PE 18:0/18:0-PEG-2000 | 10.00 | 1.00 | 10.288 |
| 5. | Di-sodium succinic acid | Q.s to pH 6.0 | Q.s to pH 6.0 | 2.0576 |
| 6. | 1% Glycine solution | Q.s to 1 mL | Q.s to 100% | 10.288 |

Manufacturing Process
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid PE 18:0/18:0-PEG-2000 was transferred and stirred for 15 minutes at 450 rpm to obtain a clear solution.

3. To the above solution dispensed quantity of duloxetine was added and stirred for 30 minutes at 400 rpm for obtaining a clear solution.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.0±0.1 using disodium succinic acid.
7. Final volume of the bulk solution was adjusted to desired level with remaining amount of 1% glycine solution.
8. The bulk solution was lyophilized after filling into vials.

Example 8

| | | Example 8A | | | Example 8 B | | |
|---|---|---|---|---|---|---|---|
| S. No | Ingredients | Qty (mg/mL) | Qty % w/v | Qty % w/w | Qty (mg/mL) | Qty % w/v | Qty % w/w |
| 1. | Duloxetine Hydrochloride | 30.00 | 3.00 | 31.40 | 30.0 | 3.0 | 30.86 |
| 2. | Mannitol | 45.00 | 4.50 | 47.10 | 45.0 | 4.50 | 46.29 |
| 3. | EDTA | 0.20 | 0.02 | 0.20 | 0.20 | 0.02 | 0.205 |
| 4. | Soy lecithin (Lipoid S 100) | 10.00 | 1.00 | 10.468 | 10.0 | 1.00 | 10.28 |
| 5. | L-Histidine | 0.32 | 0.03 | 0.34 | — | — | — |
| 6. | Disodium Succinate | — | — | — | 2.000 | 0.20 | 2.057 |
| 7. | 1% Glycine solution | Q.s to 1 mL | Q.s to 100% | 10.46 | Q.s to 1 mL | Q.s to 100% | 10.28 |

Note:
pH of the formulation: 5.5 to 6.5

Manufacturing Process

Example 8A Manufacturing Process

1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid S 100 was transferred and stirred for 15 minutes at 450 rpm to obtain a clear solution.
3. To the above solution dispensed quantity of duloxetine was added and stirred for 30 minutes at 400 rpm for obtaining a clear solution.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.0±0.1 using L-histidine.
7. Final volume of the bulk solution was adjusted to desired level with remaining amount of 1% glycine solution.
8. The bulk solution was lyophilized after filling into vials.

Example 8B Manufacturing Process

1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid S 100 was transferred and stirred for 15 minutes at 450 rpm to obtain a clear solution.
3. To the above solution dispensed quantity of duloxetine was added and stirred for 30 minutes at 400 rpm for obtaining a clear solution.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.0±0.1 using disodium succinate.
7. Final volume of the bulk solution was adjusted to desired level with remaining amount of 1% glycine solution.
8. The bulk solution was lyophilized after filling into vials.

The formulation made as per the composition of 8A is tested for stability. The data at the end of 6 months is tabulated below. The data clearly shows that each individual impurity is less than 0.5% even at accelerated conditions after 6 months.

TABLE 7

Stability data of 8A formulation.
Duloxetine Hydrochloride Injection

| | Condition | | | | |
|---|---|---|---|---|---|
| | Initial | 6 M-2-8° C. | 6 M-25° C. Strength 30 mg/Vial | 6 M-30° C. | 6 M-40° C. |
| 1. Description | White lyophilized cake | White lyophilized cake | White lyophilized cake | White lyophilized cake | Light Yellow color |
| pH | 6.26 | 6.07 | 5.99 | 5.93 | 5.26 |
| Water Content (mg/vial) | NA | 0.4 | 0.9 | 0.5 | 1.3 |
| 2. Assay (%) | 104.7 | 104.3 | 100.6 | 101.5 | 102.9 |
| 3. Impurity Name | | | | | |
| Duloxetine Alcohol | 0.00 | ND | ND | ND | 0.01 |
| Duloxetine 4-Napthyl isomer | 0.01 | 0.01 | 0.01 | 0.01 | 0.01 |
| Alpha Napthol | 0.00 | 0.01 | 0.02 | 0.02 | 0.06 |
| Duloxetine Beta napthol-1-yl isomer | 0.01 | 0.01 | 0.01 | 0.01 | 0.01 |
| 4. Total Impurities (%) | 0.10 | 0.10 | 0.13 | 0.14 | 0.40 |

Example 9

| S. No | Ingredients | Qty (mg/5 mL) | Qty (mg/mL) | Qty % w/v | Qty % w/w |
|---|---|---|---|---|---|
| 1. | Duloxetine Hydrochloride | 30.00 | 6.00 | 0.60 | 8.54 |
| 2. | Pregabalin | 75.0 | 15.0 | 1.50 | 21.35 |
| 3. | Mannitol | 185 | 37 | 3.70 | 52.68 |
| 4. | EDTA | 0.20 | 0.04 | 0.004 | 0.05 |
| 5. | Soy lecithin (Lipoid S 100) | 10.0 | 2.00 | 0.20 | 2.84 |
| 6. | L-Histidine | 0.96 | 0.19 | 0.019 | 0.27 |
| 7. | 1% Glycine solution | Q.s to 5 mL | Q.s To 1 mL | Q.s to 100% | 14.23 |

Manufacturing Process
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid S 100 was transferred and stirred for 15 minutes at 450 rpm to obtain a clear solution.
3. To the above solution dispensed quantity of duloxetine was added and stirred for 30 minutes at 400 rpm for obtaining a clear solution, followed by addition of pregabalin and stirred well for 15 minutes at 400 rpm until a clear solution is obtained.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.5±0.1 using L-histidine.
7. Final volume of the bulk solution was adjusted to desired level with remaining amount of 1% glycine solution.
8. The bulk solution was lyophilized after filling into vials.

Example 10

| S. No | Ingredients | Qty (mg/1 mL) | Qty % w/v | Qty % w/w |
|---|---|---|---|---|
| 1. | Duloxetine Hydrochloride | 30.0 | 3.0 | 15.34 |
| 2. | Gabapentin | 100.0 | 10.0 | 51.14 |
| 3. | Mannitol | 45.00 | 4.50 | 23.01 |
| 4. | EDTA | 0.20 | 0.02 | 0.10 |
| 5. | Soy lecithin (Lipoid S 100) | 10.00 | 1.00 | 5.11 |
| 6. | L-Histidine | 0.32 | 0.033 | 0.16 |
| 7. | 1% Glycine solution | Q.s to 1 mL | Q.s to 100% | 5.11 |

Manufacturing Process
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid S 100 was transferred and stirred for 15 minutes at 450 rpm to obtain a clear solution.
3. To the above solution dispensed quantity of duloxetine was added and stirred for 30 minutes at 400 rpm for obtaining a clear solution, followed by addition of gabapentin and stirred well for 15 minutes at 400 rpm until a clear solution is obtained.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.5±0.1 using L-histidine.
7. Final volume of the bulk solution was adjusted to desired level with remaining amount of 1% glycine solution.
8. The bulk solution was lyophilized after filling into vials.

Example 11

| S. No | Ingredients | Example 11A | | | | Example 11B | | | |
|---|---|---|---|---|---|---|---|---|---|
| | | Qty (mg/20 mL) | Qty (mg/mL) | Qty % w/v | Qty % w/w | Qty (mg/20 mL) | Qty (mg/mL) | Qty % w/v | Qty % w/w |
| 1. | Duloxetine Hydrochloride | 30.00 | 1.50 | 0.30 | 2.66 | 30.00 | 1.50 | 0.30 | 3.22 |
| 2. | Dexamethasone sodium phosphate | 8.00 | 0.40 | 0.08 | 0.711 | 12.00 | 0.60 | 0.12 | 1.29 |
| 3. | Mannitol | 875.00 | 43.75 | 4.37 | 77.74 | 875.00 | 43.75 | 4.37 | 94.10 |
| 4. | EDTA | 0.20 | 0.01 | 0.002 | 0.017 | 0.20 | 0.01 | 0.002 | 0.021 |
| 5. | Soy lecithin (Lipoid S 100) | 10.00 | 0.50 | 0.10 | 0.88 | 10.0 | 0.50 | 0.10 | 1.075 |
| 6. | L-Histidine | 2.36 | 0.118 | 0.011 | 0.20 | 2.59 | 0.12 | 0.012 | 0.27 |
| 7. | 1% Glycine solution | Q.s to 20 mL | Q.s to 1 mL | Q.s to 100% | 17.768 | Q.s to 10 mL | Q.s to 1 mL | Q.s to 100% | 3.22 |

Note:
pH of the formulation: 7.5-8.5

Manufacturing Process
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid S 100 was transferred and stirred for 15 minutes at 450 rpm to obtain a clear solution.
3. To the above solution dispensed quantity of duloxetine was added and stirred for 30 minutes at 400 rpm for obtaining a clear solution, followed by addition of dexamethasone sodium phosphate and stirred well for 45 minutes at 400 rpm until a clear solution is obtained.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 7.8±0.1 using L-histidine.
7. Final volume of the bulk solution was adjusted to desired level with remaining amount of 1% glycine solution.
8. The bulk solution was lyophilized after filling into vials.

Manufacturing Process
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid S 100 was transferred and stirred for 15 minutes at 450 rpm to obtain a clear solution.
3. To the above solution dispensed quantity of duloxetine was added and stirred for 30 minutes at 400 rpm for obtaining a clear solution, followed by addition of Diclofenac Sodium and stirred well for 45 minutes at 400 rpm until a clear solution is obtained.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.5±0.1 using L-histidine.
7. Final volume of the bulk solution was adjusted to desired level with remaining amount of 1% glycine solution.
8. The bulk solution was lyophilized after filling into vials.

Example 12

| S. No | Ingredients | Qty (mg/25 mL) | Qty (mg/mL) | Qty % w/v | Qty % w/w |
|---|---|---|---|---|---|
| 1. | Duloxetine Hydrochloride | 30.00 | 1.20 | 0.12 | 2.39 |
| 2. | Diclofenac Sodium | 37.50 | 1.50 | 0.15 | 2.99 |
| 3. | Mannitol | 920.00 | 36.80 | 3.68 | 73.36 |
| 4. | EDTA | 0.20 | 0.01 | 0.001 | 0.019 |
| 5. | Soy lecithin (Lipoid S 100) | 10.00 | 0.40 | 0.04 | 0.79 |
| 6. | L-Histidine | 6.24 | 0.24 | 0.024 | 0.49 |
| 7. | 1% Glycine solution | Q.s to 25 mL | Q.s to 1 mL | Q.s to 100% | 19.936 |

Example 13

| S. No | Ingredients | Qty (mg/50 mL) | Qty (mg/mL) | Qty % w/v | Qty % w/w |
|---|---|---|---|---|---|
| 1. | Duloxetine Hydrochloride | 30.00 | 0.60 | 0.060 | 1.0375 |
| 2. | Paracetamol | 500.00 | 10.00 | 1.000 | 17.291 |
| 3. | Mannitol | 1835.00 | 36.70 | 3.670 | 63.46 |
| 4. | EDTA | 0.20 | 0.00 | 0.000 | 0.0069 |
| 5. | Soy lecithin (Lipoid S 100) | 10.00 | 0.20 | 0.020 | 0.346 |
| 6. | L-Histidine | 16.4 | 0.328 | 0.0328 | 0.567 |
| 7. | 1% Glycine solution | Q.s to 50 mL | Q.s to 1 mL | Q.s to 100% | 17.29 |

25

Manufacturing Process
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid S 100 was transferred and stirred for 15 minutes at 450 rpm to obtain a clear solution.
3. To the above solution dispensed quantity of duloxetine was added and stirred for 30 minutes at 400 rpm for obtaining a clear solution, followed by addition of paracetamol and stirred well for 60 minutes at 400 rpm until a clear solution is obtained.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.0±0.1 using L-histidine.
7. Final volume of the bulk solution was adjusted to desired level with remaining amount of 1% glycine solution.
8. The bulk solution was lyophilized after filling into vials.

Example 14

| S. No | Ingredients | Qty (mg/mL) | Qty % w/v | Qty (w/w) |
|---|---|---|---|---|
| 1. | Duloxetine Hydrochloride | 30.00 | 3 | 15.343 |
| 2. | Lidocaine HCl | 100.00 | 10 | 51.143 |
| 3. | Mannitol | 45.00 | 4.5 | 23.015 |
| 4. | EDTA | 0.20 | 0.02 | 0.1023 |
| 5. | Lipoid PE 18:0/18:0-PEG-2000 | 10.00 | 1.00 | 5.1144 |
| 6. | L-Histidine | Q.s to pH 6.0 | Q.s to pH 6.0 | 0.168 |
| 7. | 1% Glycine solution | Q.s to 1 mL | Q.s to 100% | 5.12 |

Manufacturing Process
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid PE 18:0/18:0-PEG-2000 was transferred and stirred for 15 minutes at 450 rpm to obtain a clear solution.
3. To the above solution dispensed quantity of duloxetine was added and stirred for 30 minutes at 400 rpm for obtaining a clear solution, followed by addition of lidocaine hydrochloride and stirred well for 30 minutes at 400 rpm until a clear solution is obtained.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.0±0.1 using L-histidine.
7. Final volume of the bulk solution was adjusted to desired level with remaining amount of 1% glycine solution.
8. The bulk solution was lyophilized after filling into vials.

Example 15

| S. No | Ingredients | Qty (mg/mL) | Qty % w/v | Qty % w/w |
|---|---|---|---|---|
| 1. | Duloxetine Hydrochloride | 30.00 | 3 | 15.21 |
| 2. | Lidocaine HCl | 100.0 | 10 | 50.71 |
| 3. | Mannitol | 45.0 | 4.5 | 22.8 |
| 4. | EDTA | 0.20 | 0.02 | 0.10 |
| 5. | Lipoid PE 18:0/18:0-PEG-2000 | 10.0 | 1.0 | 5.07 |
| 6. | Di-sodium succinic acid | Q.s to pH 6.0 | Q.s to pH 6.0 | 1.01 |
| 7. | 1% Glycine solution | Q.s to 1 mL | Q.s to 100% | 5.07 |

Manufacturing Procedure
1. Preparation of 1% Glycine solution: Required quantity of ultrapure water was taken in a stainless steel vessel to which desired quantity of Glycine was added to get 1% w/v solution.
2. Preparation of Bulk solution: 80% of glycine solution required was taken in a manufacturing vessel to which dispensed quantity of Lipoid PE 18:0/18:0-PEG-2000 was transferred and stirred for 15 minutes at 450 rpm to obtain a clear solution.
3. To the above solution dispensed quantity of duloxetine was added and stirred for 30 minutes at 400 rpm for obtaining a clear solution, followed by addition of Lidocaine hydrochloride and stirred well for 30 minutes at 400 rpm until a clear solution is obtained.
4. Dispensed quantity of Mannitol was added to the above solution and stirred for 30 minutes at 400 rpm to get a clear solution.
5. Required quantity of EDTA was transferred to the manufacturing vessel and stirred for 15 minutes at 400 rpm to get clear solution.
6. pH of the above bulk solution was adjusted to pH 6.0±0.1 using disodium succinic acid.
7. Final volume of the bulk solution was adjusted to desired level with remaining amount of 1% glycine solution.
8. The bulk solution was lyophilized after filling into vials.

Example 16

| S. No | Ingredients | Qty (mg/mL) | Qty % w/v | Qty % w/w |
|---|---|---|---|---|
| 1. | Duloxetine Hydrochloride | 30.00 | 3.00 | 31.40 |
| 2. | Mannitol | 45.00 | 4.50 | 47.10 |
| 3. | EDTA | 0.20 | 0.02 | 0.20 |
| 4. | Egg lecithin (Lipoid E80S) | 10.00 | 1.00 | 10.46 |
| 5. | L-Histidine | 0.32 | 0.03 | 0.34 |

-continued

| S. No | Ingredients | Qty (mg/mL) | Qty % w/v | Qty % w/w |
|---|---|---|---|---|
| 6. | 1% Glycine solution | Q.s to 1 mL | Q.s to 100% | 10.46 |

Manufacturing Process
1. Preparation of 1% glycine solution: Required quantity of glycine was dissolved in required quantity of water.
2. Preparation of Bulk solution: 80% of glycine solution required for the batch was taken in a manufacturing vessel to which required quantity of Lipoid E80S was transferred and stirred to obtain a clear solution.
3. To the above solution required quantity of duloxetine was added and stirred to get clear solution.
4. Required quantity of Mannitol was added to the above solution and stirred to get a clear solution.
5. Required quantity of EDTA was transferred to the above solution and stirred to get clear solution.
6. pH of the above bulk solution adjusted to pH 6.0±0.1 using L-histidine.
7. Final volume of the bulk solution was adjusted with remaining amount of 1% glycine solution.
8. The bulk solution was filtered and filled into vials and were then partially stoppered with single slotted lyo stopper and subjected for lyophilisation.
9. After lyophilisation the vials were stoppered completely under vacuum and were sealed with aluminium tear off seals after unloading.

Example 17

| S. No | Ingredients | Qty (mg/mL) | Qty % w/v | Qty % w/w |
|---|---|---|---|---|
| 1. | Duloxetine Hydrochloride | 30.00 | 3.00 | 31.40 |
| 2. | Mannitol | 45.00 | 4.50 | 47.10 |
| 3. | EDTA | 0.20 | 0.02 | 0.20 |
| 4. | HPBCD (Hydroxypropyl Beta cyclodextrin) | 10.00 | 1.00 | 10.46 |
| 5. | L-Histidine | 0.32 | 0.03 | 0.34 |
| 6. | 1% Glycine solution | Q.s to 1 mL | Q.s to 100% | 10.46 |

Manufacturing Process
1. Preparation of 1% glycine Solution: Required quantity of glycine was dissolved in required quantity of water.
2. Preparation of Bulk Solution: 80% of glycine solution required for the batch was taken in a manufacturing vessel to which required quantity of HPBCD was transferred and stirred obtain a clear solution.
3. To the above solution required quantity of duloxetine was added and stirred to get clear solution.
4. Required quantity of Mannitol was added to the above solution and stirred to get a clear solution.
5. Required quantity of EDTA was transferred to the above solution and stirred to get clear solution.
6. pH of the above bulk solution adjusted to pH 6.0±0.1 using L-histidine.
7. Final volume of the bulk solution was adjusted with remaining amount of 1% glycine solution.
8. The bulk solution was filtered and filled into vials and were then partially stoppered with single slotted lyo stopper and subjected for lyophilisation.
9. After lyophilisation the vials were stoppered completely under vacuum and were sealed with aluminium tear off seals after unloading.

Example 18: Compositions of Duloxetine API Solution Prepared in Phosphate Buffer pH 6.4 (Used as Control in the Study)

| S. No | Material name | Qty (mg/mL) | Qty % w/v | Qty % w/w |
|---|---|---|---|---|
| 1. | Duloxetine Hydrochloride | 30.00 | 3.00 | 2.94 |
| 2. | Phosphate Buffer pH 6.8 | Q.s to 1 mL | Q.s to 100% | 97.06 |

Manufacturing Process
1. 80% of Phosphate buffer pH 6.8 required for the batch was taken in a SS vessel.
2. Required quantity of Duloxetine API was dispensed and transferred to the above vessel and dissolved with stirring for 10 minutes at 300 rpm.
3. Ensuring the clarity of the solution the volume was adjusted with remaining amount of Phosphate buffer.

What is claimed is:

1. A lyophilized parenteral formulation consisting essentially of duloxetine hydrochloride, and one or more pharmaceutically acceptable excipients, wherein a content of Duloxetine Alcohol, Duloxetine Napthol 4-yl isomer, Alpha Napthol and Duloxetine Beta napthol-1-yl isomer individually is less than 0.5% w/w.

2. The formulation of claim 1, wherein the one or more pharmaceutically acceptable excipients are selected from the group consisting of a bulking agent, a buffer, a stabilizer, and a surfactant.

3. The formulation of claim 2, wherein the bulking agent is selected from the group consisting of mannitol, dextrose, cyclodextrin, sodium chloride and sorbitol.

4. The formulation of claim 2, wherein the buffer is selected from the group consisting of acetate buffer, phosphate buffer, aspartic acid and boric acid buffer, citrate buffer, glycine buffer, histidine buffer, succinate buffer, alanine buffer, valine buffer, and lactic acid buffer.

5. The formulation of claim 2, wherein the surfactant is selected from the group consisting of lecithin, soya lecithin, egg lecithin, PEG-PE and phosphatidyl choline or mixtures thereof.

6. The formulation of claim 2, wherein the stabilizer is selected from the group consisting of DOTA, DTPA and EDTA.

7. The formulation of claim 1, further comprising one or more bulking agents selected from the group consisting of mannitol and cyclodextrin.

8. The formulation of claim 7, further comprising: one or more of glycine and histidine.

9. The formulation of claim 8, further comprising: one or more stabilizers selected from the group consisting of DOTA, DTPA and EDTA.

10. A kit comprising (i) a vial comprising lyophilized parenteral formulation of claim 1, and (ii) a vial comprising a diluent for reconstitution.

11. The kit of claim 10, wherein the diluent is selected from the group consisting of water for injection, dextrose solution, normal saline, mannitol solution, dextrose normal saline solution and half saline solution.

12. The kit of claim 10, further comprising one or more bulking agents selected from the group comprising mannitol, dextrose, cyclodextrin, sodium chloride and sorbitol,
one or more of glycine and histidine, and
one or more stabilizers selected from the group consisting of DOTA, DTPA and EDTA.

13. A method of treatment for preoperative, perioperative or post-operative pain, comprising administering the formulation of claim 1 to a patient in need thereof.

14. The formulation of claim 9, wherein the bulking agent is selected from the group consisting of dextrose, cyclodextrin, sodium chloride and sorbitol.

15. A parenteral formulation comprising:
(i) duloxetine hydrochloride,
(ii) one or more bulking agents selected from the group consisting of mannitol and cyclodextrin,
(iii) one or more buffers selected from the group consisting of glycine and histidine, and
(iv) one or more stabilizers selected from the group consisting of DOTA, DTPA and EDTA,
wherein a content of Duloxetine Alcohol, Duloxetine Napthol 4-yl isomer, Alpha Napthol and Duloxetine Beta napthol-1-yl isomer individually is less than 0.5% w/w.

\* \* \* \* \*